United States Patent [19]

Dirina

[11] Patent Number: 5,342,311
[45] Date of Patent: Aug. 30, 1994

[54] SKIN SHIELD FOR PROTECTION AGAINST ACCIDENTAL NEEDLE PUNCTURE

[76] Inventor: John G. Dirina, 3828 Norbrook Dr., Columbus, Ohio 43220-4705

[21] Appl. No.: 70,779

[22] Filed: Jun. 3, 1993

[51] Int. Cl.⁵ .............................................. A61M 5/00
[52] U.S. Cl. ..................................... 604/116; 128/919
[58] Field of Search ................ 128/919; 604/115–117, 604/187, 192, 263, 289–290, 310–311

[56]     References Cited
         U.S. PATENT DOCUMENTS

| | | | |
|---|---|---|---|
| 4,031,890 | 6/1977 | Homan . | |
| 4,586,924 | 5/1986 | Lanning | 604/115 |
| 4,758,229 | 7/1988 | Doerschner . | |
| 4,840,618 | 6/1989 | Marvel . | |
| 4,898,588 | 2/1990 | Roberts . | |
| 4,900,309 | 2/1990 | Netherton et al. | 604/192 |
| 4,986,817 | 1/1991 | Code | 604/192 |
| 5,061,248 | 10/1991 | Sacco | 604/192 |
| 5,078,694 | 1/1992 | Wallace | 604/192 |
| 5,123,907 | 6/1992 | Romaine | 604/131 |
| 5,156,426 | 10/1992 | Graves | 294/1.1 |
| 5,171,228 | 12/1992 | McDonald | 604/175 |
| 5,224,940 | 7/1993 | Dann et al. | 604/290 |
| 5,248,301 | 9/1993 | Koenig, Jr. et al. | 604/164 |

FOREIGN PATENT DOCUMENTS 303824  2/1989  European Pat. Off. ............ 604/116

*Primary Examiner*—John D. Yasko
*Assistant Examiner*—Corrine Maglione

[57]     ABSTRACT

A skin shield device for protecting users (to include caregivers and patients) from accidental needle stick or puncture (hereinafter needle stick). The skin shield device is to be used by users who are removing a needle from an subcutaneously implanted vascular access device (hereinafter port) injection area (hereinafter site). The skin shield body is comprised of a substantially flexible annular disc with finger tabs and a central shield opening. The finger tabs are used to apply pressure at a port site. The pressure at the port site is to secure and stabilize the port site for safe needle removal. The central shield opening is slipped over and around a needle to surround and stabilize the port site. Once the central shield opening is in place around the site, pressure is applied downward by a user's fingers applying downward force at the finger tabs. The downward pressure causes the shield body to stabilize the port site during needle removal. The port contains a rubber septum into which injections are made. Needle rebound results when a needle binds against the port's rubber septum upon needle removal from the port. The shield body is of sufficient thickness to be resistant to needle penetration. The resistance to needle penetration protects a user from accidental needle stick in the case of downward needle rebound. By applying pressure at the finger tabs, a user's fingers are kept away from the port site during needle removal, and keeping a user's fingers away from the port site decreases the risk of accidental rebound needle stick.

3 Claims, 2 Drawing Sheets

SKIN SHIELD FOR PROTECTION AGAINST ACCIDENTAL NEEDLE PUNCTURE

BACKGROUND AND SUMMARY

The device relates to a skin shield device, consisting of a substantially flexible disc, finger tabs, and a central shield opening. The skin shield device is comprised of a material resistant to needle penetration. The skin shield device is used to protect users (to include caregivers and patients) from accidental needle stick or puncture (hereinafter needle stick) while involved in removing a needle from a subcutaneously implanted vascular access device (hereinafter port).

In modern medical practice, many patients who receive long-term intravenous therapy require the use of a port. The port is attached to the patient's blood supply by means of a catheter. One end of the catheter is attached to the port, the other end of the catheter is inserted into a patient's blood vessel. The port contains a rubber or rubber-like diaphragm injection site (hereinafter septum) into which injections are made. Injections are made through the patient's skin and into a septum of a port. Indirect access to the patient's blood supply saves the patient's blood vessels from trauma associated with repeated, direct injections into blood vessels.

A user who gives an injection into the port does so by first stabilizing and securing the port between the user's thumb and forefingers. Because the port is implanted under a layer of the patient's skin, the user must also stabilize and secure the skin layer which covers the port. The user's thumb and fingers are directly within the port injection area and are subject to accidental needle stick during the removal of the needle from the port septum. The port injection area (hereinafter site) is the area from which the inserted needle used for injection is removed, meant to include both the septum and skin layer.

The needle is removed from both the port site upon completion of the injection. The thickness of the rubber used in the port septum can create a frictional resistance to needle removal. The frictional resistance causes the needle to bind against the port septum upon withdrawal. The frictional resistance compels the user to withdraw the needle from the port septum by means of a controlled, steadily increasing, upward and downward force (hereinafter tension force). The object of using tension force is to remove the needle from the port septum without injuring the patient or damaging the port. The result of using tension force is that upon total withdrawal of the needle from the port site, a downward rebound of the needle results which can cause needle stick to either the user's skin or fingers.

SUMMARY

The present invention relates to a skin shield, comprising a substantially flexible plate having an opening formed through a central region of the plate. In view of the foregoing, it is the object of the present invention to provide a device by which the user can stabilize and secure a subcutaneously implanted port while keeping the user's fingers away from the port injection area. The port site is the area into which the needle used for injection is removed from the septum and skin layer. The size of the port site is defined by the size of the port and port septum and includes the skin layer covering the port.

The skin shield can reduce the risk of accidental needle stick to the user. The skin shield device is composed of a material of sufficient thickness to make it resistant to needle penetration. Owing to its resistance to needle penetration, the flexible disc of the skin shield's body that covers the area around the port site can protect the patient from accidental needle stick caused by downward needle rebound toward the port.

The above and other objects and advantages will become more apparent when taken in conjunction with the following detailed description and drawings.

IN THE DRAWING

DETAILED DESCRIPTION OF THE SKIN SHIELD DEVICE

Figure 1:
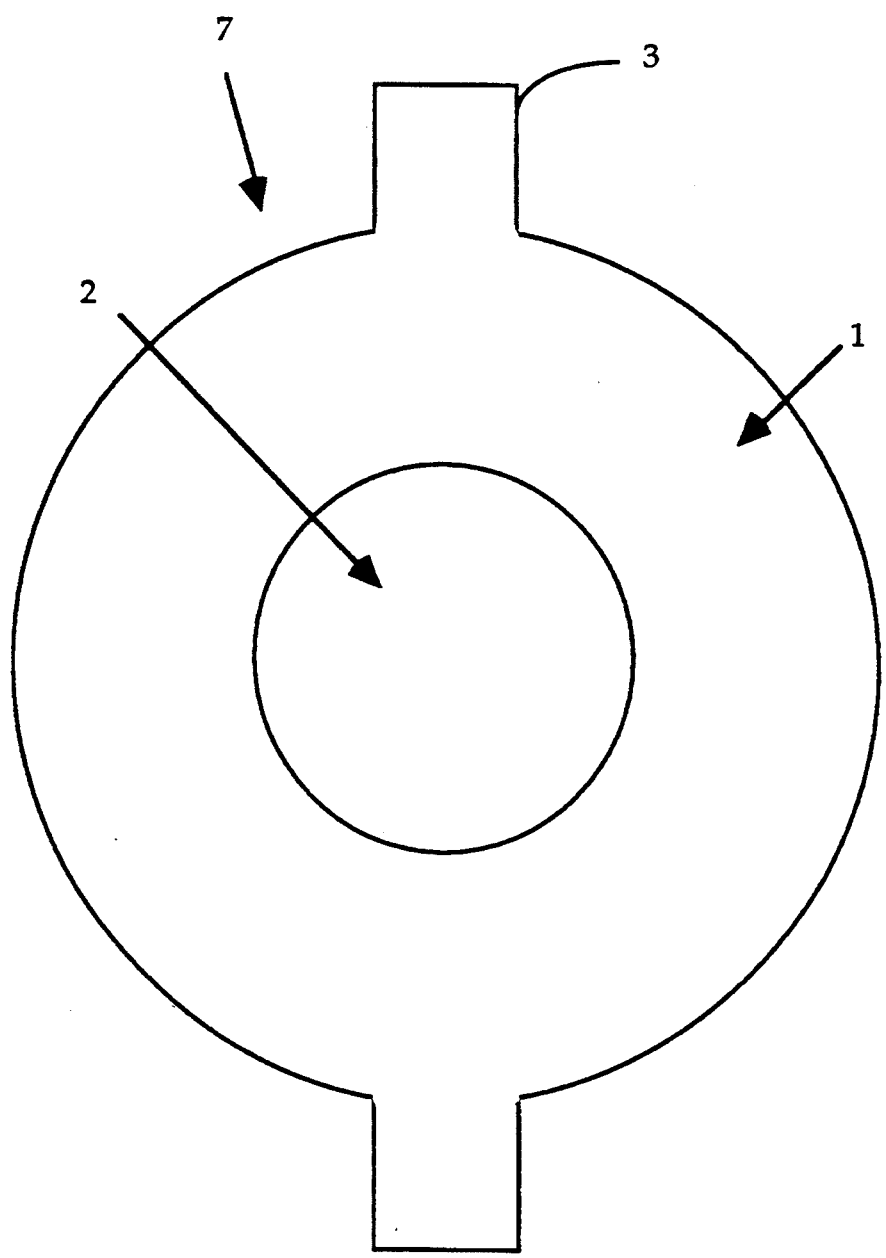
FIG. 1 is a top view depicting the preferred skin shield device having a shield body, finger tabs, and a central shield opening.

FIG. 1 depicts the preferred embodiment of a skin shield 7 comprising a flexible shield body 1, outlying finger tabs 3, and a central opening in the shield (hereinafter central shield opening) 2 which allows the shield to be slipped into position over and around the port site. The skin shield 7 comprising a substantially flexible plate, where substantially flexible is defined as flexible enough to conform to the general shape of a body against which the skin shield is pressed. The finger tabs 3 are attached to the outer perimeter of the shield body 1 and are preferably spaced 180° apart.

The skin shield 7 is a plate, preferably a planar annular disc, comprised of material of sufficient thickness to allow resistance to needle penetration. The preferred skin shield 7 is approximately 0.5 millimeter in thickness and has a shield body 1 diameter of 11.25 centimeters across, finger tab 3 dimensions of 1.875 centimeters by 1.875 centimeters, and a central shield opening 2 is approximately 2.5 centimeters to 5 centimeters in diameter on center.

Figure 2:
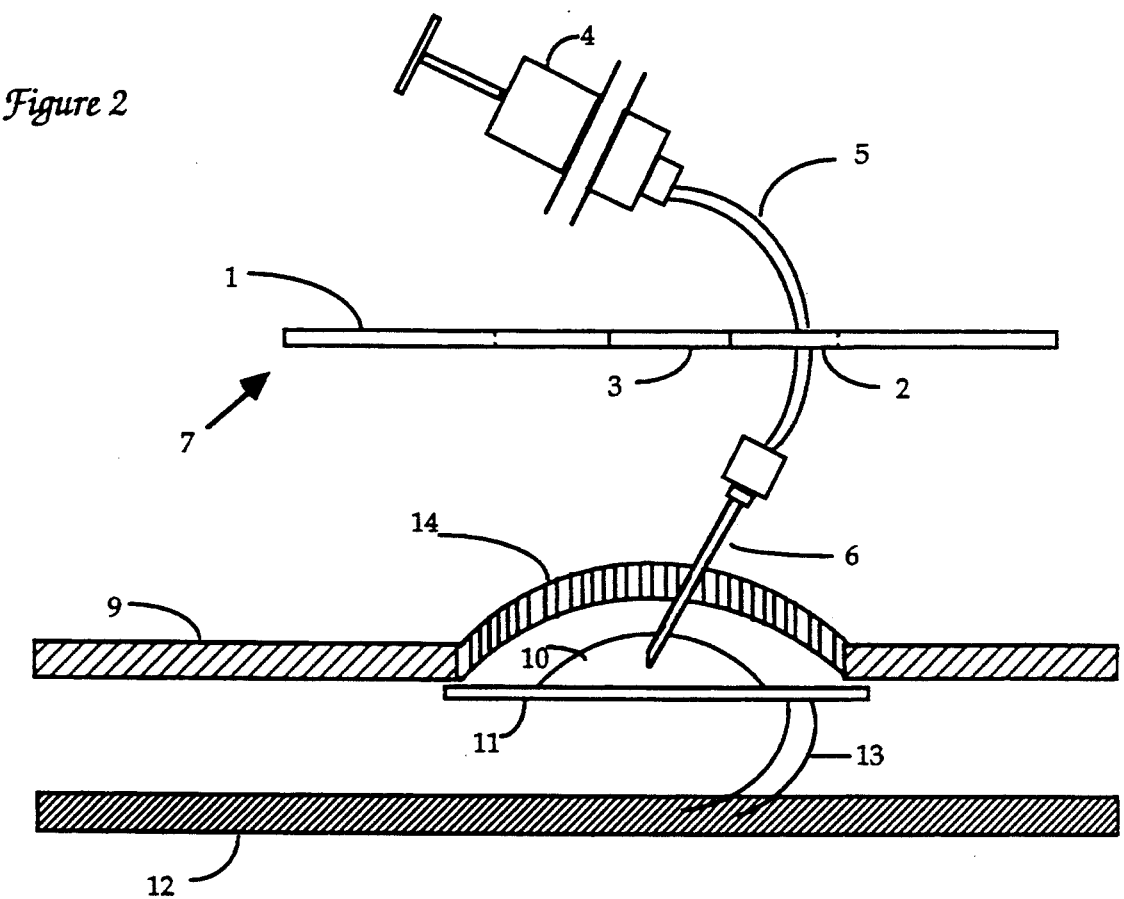
FIG. 2 is a side view depicting a skin shield in its operable position.

The side view in FIG. 2 shows how the the central shield opening 2 can be slipped over and around a syringe 4, tubing 5, and needle 6, and can be positioned over and around the port site 14. Downward stabilizing pressure can be applied at the port site 14 by using finger pressure on the finger tabs 3. The port 11 with its rubber septum 10 is implanted under the skin layer 9, and connected, by means of a catheter 13, to the blood vessel 12 of the patient. The other end of the catheter 13 is connected to the port 11.

The port 11 contains a rubber septum 10 into which injections are made. Injections are made through the patient's skin and into the septum 10 of the port 11. A user who gives an injection into the septum 10 does so by first stabilizing and securing the port 11 between the user's thumb and forefingers. Because the port 11 is implanted under a layer of the patient's skin 9, the user must also stabilize and secure the skin layer 9 which covers the port 11. The user's thumb and fingers are, therefore, in direct contact with the port site 14 and are subject to accidental needle stick during the removal of the needle 6 from the port site 14.

The needle 6 is removed from the port site upon completion of the injection. The thickness of the rubber used in the septum 10 can create a frictional resistance to needle removal. The frictional resistance causes the needle to bind against the septum 10 upon withdrawal.

The frictional resistance compels the user to withdraw the needle from the port septum using tension force. The object of using tension force is to remove the needle from the port site 14 without injuring the patient or damaging the port 11. The result of using tension force is that upon completed withdrawal of a needle 6 from the port site 14, a downward rebound of the needle 6 occurs. Needle rebound is caused by a frictional resistance to needle removal created when trying to remove the needle 6 from the port's septum 10. The needle rebound can cause needle stick in either the user's skin or fingers. The shield body 1 that surrounds the central shield opening 2 covers the patient's skin 9 that lays over the port 11. The skin 9 comprises part of the port site 14.

The preferred skin shield device 7 is comprised of a substantially flexible shield body 1 with finger tabs 3 that are attached to the outer perimeter of the shield body 1 and are spaced 180° apart. Finger pressure on the finger tabs 3 is used to apply pressure at the port site 14. The central shield opening 2 is slipped over the needle 6 to surround and define the port site 14. Once the skin shield's 7 central shield opening 2 is in place over and around the port site 14, pressure is applied downward at the finger tabs 3 causing the shield body 1 to stabilize and secure the port site 14 for needle 6 removal. By applying pressure at the finger tabs 3, the user's fingers are kept away from the port site 14, decreasing the risk of accidental needle stick.

The skin shield 7 is designed to protect a user from accidental needle stick. The skin shield device 7 is made up of a material resistant to needle penetration. The needle penetration resistance of the skin shield 7 protects the user from accidental needle stick which can result from needle rebound. To protect against accidental needle stick due to rebound, the central shield opening is in slipped over and around the port site, and the user applies downward pressure at the finger tabs. The finger tabs of the skin shield device are used to allow the user to apply downward pressure at and around the port site. Pressure is applied by the user's finger tips pushing downward on the finger tabs. By pushing downward on the finger tabs with the fingertips, the shield body is caused to stabilize and secure the port site for needle removal. The finger tabs are also used to keep the user's fingers away from the central shield opening and port site in order to prevent accidental needle stick or puncture.

An important aspect of the skin shield device is that it can be used to protect users who are involved in removing a needle from a port site from accidental needle stick or puncture. Reduced accidental needle sticks can reduce the transmission of blood borne diseases and prevent unwanted needle injury to the user.

The skin shield device is inexpensive and simple to use. The shield's light construction and compact size make it such that it can be easily carried in the user's pocket for ready and available for use.

I claim:

1. A skin shield, comprising a substantially flexible, contour conforming, penetration resistant plate having an opening formed through a central region of the plate, wherein the plate is a planar, annular disc, wherein at least two finger tabs are attached to the outer edge of the disc, extending radially outwardly from, and co-planar to, the annular disc.

2. An annular disc in accordance with claim 1 wherein the disc is approximately 0.5 millimeter in thickness, has a diameter of 11.25 centimeters across, finger tab dimensions of 1.875 centimeters by 1.875 centimeters, and a central shield opening diameter between 3.8 centimeters and 5 centimeters.

3. A method of using a skin shield that is a substantially flexible planar plate having an opening formed through a central region of the plate, the method comprising:
   a. slipping the central shield opening over and around an injection needle that is inserted into a subcutaneously implanted vascular access port;
   b. surrounding and defining a port injection site with the central shield opening;
   c. covering the skin surrounding the port site with the shield body that surrounds the central shield opening;
   d. projecting the port site through the central shield opening; and
   e. removing the injection needle from the port site through the central shield opening; while applying pressure at and around the port site by means of a user's finger tips applying downward pressure at a pair of finger tabs attached to the outer edge of the shield body, causing the shield body to stabilize and secure the port site needle removal.

* * * * *